United States Patent
Dunn et al.

(12) 
(10) Patent No.: US 6,228,332 B1
(45) Date of Patent: May 8, 2001

(54) DEACTIVATION OF ORGANISMS USING HIGH-INTENSITY PULSED POLYCHROMATIC LIGHT

(75) Inventors: Joseph E. Dunn, Vista; Reginald Wayne Clark, Del Mar; Andrew H. Bushnell; Kenton J Salisbury, both of San Diego, all of CA (US)

(73) Assignee: PurePulse Technologies, San Diego, CA (US)

( * ) Notice: Subject to any disclaimer, the term of this patent is extended or adjusted under 35 U.S.C. 154(b) by 0 days.

(21) Appl. No.: 09/025,210

(22) Filed: Feb. 18, 1998

Related U.S. Application Data

(60) Division of application No. 08/741,560, filed on Oct. 31, 1996, now Pat. No. 5,900,211, which is a continuation-in-part of application No. 08/548,453, filed on Oct. 26, 1995, now abandoned.

(30) Foreign Application Priority Data

Feb. 27, 1997 (JP) ...................................... 9-43472

(51) Int. Cl.⁷ ............................... B01J 19/08; B01J 19/12
(52) U.S. Cl. ........................... 422/186.3; 422/22; 422/23; 422/24; 210/748
(58) Field of Search .................................. 422/186.3, 22, 422/23, 24; 210/748; 426/238, 248; 435/173.3

(56) References Cited

U.S. PATENT DOCUMENTS

| | | | |
|---|---|---|---|
| 2,072,416 | 3/1937 | Berndt et al. | ............................. 99/13 |
| 2,072,417 | 3/1937 | Berndt et al. | ............................. 99/13 |

(List continued on next page.)

FOREIGN PATENT DOCUMENTS 1946267  1/1976  (DE) .
2907887  9/1980  (DE) .
364128  12/1931  (GB) .

(List continued on next page.)

OTHER PUBLICATIONS

Johnson, "Flashblast—the light that cleans", *Popular Science*, pp. 82–84, No date Available.

(List continued on next page.)

*Primary Examiner*—Kathryn Gorgos
*Assistant Examiner*—Wesley A. Nicolas
(74) *Attorney, Agent, or Firm*—Fitch, Even, Tabin & Flannery

(57) ABSTRACT

A system of deactivating microorganisms in water involves illuminating the microorganisms using at least one short-duration, high-intensity pulse of broad-spectrum polychromatic light. The system includes a watertight housing having an inlet port and an outlet port for the flow water. A tubular light source for deactivating microorganisms and a tubular baffle for directing the water flow are positioned within the watertight housing. Waters enters the inlet port and flows between the watertight housing and the tubular baffle in one direction, around the end of the tubular baffle and back through the center of the tubular baffle in a second direction exiting the outlet port. In one embodiment, the inlet and outlet ports are positioned at the same end of the watertight housing. In a another embodiment, the inlet port is at the end of the watertight housing and the outlet port extends radially from the tubular baffle through the side of the watertight housing. Additionally, a removable recirculating hose may be connected from the inlet port to the outlet port for recirculating the water. A quartz jacket filled with a cooling material may be used around the tubular light source to provide cooling to the light source and spectral filtering of the light emitted from the light source. The inner surface of the baffle may be reflectorized to reflect light from the light source.

25 Claims, 5 Drawing Sheets

U.S. PATENT DOCUMENTS

| | | | |
|---|---|---|---|
| 2,438,168 | 3/1948 | Hearst et al. | 99/170 |
| 2,482,507 | 9/1949 | Rentschler et al. | 99/218 |
| 2,930,706 | 3/1960 | Moulton et al. | 99/186 |
| 3,814,680 | 6/1974 | Wood | 210/64 |
| 3,817,703 | 6/1974 | Atwood | 21/2 |
| 3,923,663 * | 12/1975 | Reid | 210/251 |
| 3,941,670 | 3/1976 | Pratt | 204/158 R |
| 3,955,921 | 5/1976 | Tensmeyer | 21/54 R |
| 4,042,325 | 8/1977 | Tensmeyer | 21/54 R |
| 4,112,124 | 9/1978 | Jarvis | 426/234 |
| 4,141,686 | 2/1979 | Lewis | 250/436 |
| 4,265,747 | 5/1981 | Copa et al. | 210/758 |
| 4,304,996 | 12/1981 | Blades | 250/373 |
| 4,390,432 | 6/1983 | Takeguchi | 210/748 |
| 4,433,244 | 2/1984 | Hogan | 250/455.1 |
| 4,464,336 | 8/1984 | Hiramoto | 422/24 |
| 4,479,762 | 10/1984 | Bilstad et al. | 417/395 |
| 4,534,282 | 8/1985 | Marinoza | 99/451 |
| 4,535,247 | 8/1985 | Kurtz | 250/436 |
| 4,601,822 | 7/1986 | Zamburro | 210/192 |
| 4,766,321 | 8/1988 | Lew et al. | 250/431 |
| 4,769,131 | 9/1988 | Noll et al. | 210/85 |
| 4,871,559 | 10/1989 | Dunn et al. | 426/248 |
| 4,902,411 | 2/1990 | Lin | 210/104 |
| 4,904,874 | 2/1990 | Ellner | 250/436 |
| 4,910,942 | 3/1990 | Dunn et al. | 53/425 |
| 4,952,511 | 8/1990 | Radmer | 435/314 |
| 4,968,891 | 11/1990 | Jhawar et al. | 250/438 |
| 4,971,687 * | 11/1990 | Anderson | 210/85 |
| 5,034,235 | 7/1991 | Dunn et al. | 426/238 |
| 5,037,618 | 8/1991 | Hager | 422/186 |
| 5,120,450 | 6/1992 | Stanley | 210/748 |
| 5,144,146 | 9/1992 | Wekhof | 250/492.1 |
| 5,151,252 | 9/1992 | Mass | 422/186.3 |
| 5,208,461 | 5/1993 | Tipton | 250/436 |
| 5,235,905 | 8/1993 | Bushnell et al. | 99/451 |
| 5,364,645 | 11/1994 | Lagunas-Solar et al. | 426/248 |
| 5,433,738 | 7/1995 | Stinson | 607/92 |
| 5,446,289 | 8/1995 | Shodeen et al. | 250/455.11 |
| 5,466,425 | 11/1995 | Adams | 422/186.3 |
| 5,498,394 | 3/1996 | Matschke | 422/24 |
| 5,573,666 * | 11/1996 | Korin | 210/232 |
| 5,597,482 * | 1/1997 | Melyon | 210/209 |
| 5,626,768 | 5/1997 | Ressler et al. | 210/748 |
| 5,768,853 | 6/1998 | Bushnell et al. | 53/167 |
| 5,786,812 | 11/1988 | Humphreys | 250/455.1 |
| 5,843,309 * | 12/1998 | Mancil | 210/205 |
| 5,900,211 * | 5/1999 | Dunn et al. | 422/24 |

FOREIGN PATENT DOCUMENTS

| | | |
|---|---|---|
| 1052513 | 12/1963 | (GB) . |
| 1346521 | 2/1974 | (GB) . |
| 1448411 | 9/1976 | (GB) . |
| 1548997 | 7/1979 | (GB) . |
| 1581998 | 12/1980 | (GB) . |
| 7502834 | 3/1975 | (NL) . |
| 8201703 | 5/1982 | (WO) . |
| 8803369 | 5/1988 | (WO) . |
| 8910069 | 11/1989 | (WO) . |
| 9528095 | 10/1995 | (WO) . |
| 9625048 | 8/1996 | (WO) . |

OTHER PUBLICATIONS

Rentschler, et al., "Bactericidal Effect of Ultraviolet Radiation", *Research Department, Westingtonhouse Lamp Division*, Bloomfield, New Jersey, pp. 745–774, No Date Available.

Dunn, et al., "Pulsed–Light Treatment of Food and Packaging", *Food Technology*, vol. 49, No. 9, Sep. 1, 1995, pp. 95–98.

Campbell, et al., "Inactivation of Oocysts of Cryptosprodium Parvum by Ultraviolet Irradiation", *Water Research*, vol. 29, No. 11, Nov. 1, 1995, pp. 2583–2586.

* cited by examiner

DEACTIVATION OF ORGANISMS USING HIGH-INTENSITY PULSED POLYCHROMATIC LIGHT

This is a Divisional patent application of U.S. patent application Ser. No. 08/741,560, filed Oct. 31, 1996 for, IMPROVED DEACTIVATION OF ORGANISMS USING HIGH-INTENSITY PULSED POLYCHROMATIC LIGHT, now U.S. Pat. No. 5,900,211, of Dunn, et al, which is a Continuation in Part of U.S. patent application Ser. No. 08/548,453, filed Oct. 26, 1995, for DEACTIVATION OF PROTOZOA USING HIGH-INTENSITY PULSED POLYCHROMATIC LIGHT, of Dunn et al., now abandoned, all of which are incorporated herein by reference.

BACKGROUND OF THE INVENTION

The present invention relates to disinfection or decontamination of food, water, air and packaging materials, and more particularly, is directed to deactivation or killing of organisms, such as cyst-forming protozoa, such as *Cryptosporidium parvum*, or viruses, such as poliovirus, in food, water, or air, or on packaging material. Even more particularly, the present invention relates to deactivation of such organisms using high-intensity short-duration pulses of polychromatic light in a broad spectrum.

As used herein the terms "deactivate", or decontaminate and forms thereof refer to the killing or sterilizing, i.e., rendering unable to produce, of microorganisms.

Substantial technical effort has been directed to increasing the levels of microbiological decontamination in water, air, foodstuffs and other microbiologically labile products, and packaging materials so as to preserve these products against microbiological spoilage and/or to prevent infection of their consumers. Such efforts have involved both the treatment of products and packaging material, and the development of packaging techniques for preservation.

The photobiological effects of light, including infrared light (780 nm to 2600 nm; i.e., $3.9 \times 10^{14}$ Hz to $1.2 \times 10^{14}$ Hz), visible light (380 to 780 nm; i.e., $7.9 \times 10^{14}$ Hz to $3.9 \times 10^{14}$ Hz), near ultraviolet light (300 to 380 nm; i.e., $1.0 \times 10^{15}$ Hz to $7.9 \times 10^{14}$ Hz) and far ultraviolet light (170 to 300 nm; i.e., $1.8 \times 10^{15}$ Hz to $1.0 \times 10^{15}$ Hz), have been studied, and, in particular, efforts have been made to employ light to deactivate microorganisms on food products, containers for food products or medical devices. See, e.g., U.S. Pat. Nos. 4,871,559; 4,910,942; and 5,034,235, issued to Dunn et al. (the '559, '942, and '235 patents), incorporated herein by reference.

Other studies of the photobiological effects of light are reported in Jagger, J., "Introduction to Research in Ultraviolet Photobiology", Prentice Hall, Inc., 1967. U.S. Pat. No. 2,072,417 describes illuminating substances, e.g., milk, with active rays, such as ultraviolet rays; U.S. Pat. No. 3,817,703 describes sterilization of light-transmissive material using pulsed laser light; and U.S. Pat. No. 3,941,670 describes a method of sterilizing materials, including foodstuffs, by exposing the materials to laser illumination to inactivate microorganisms. However, such methods have various deficiencies, such as limited throughput capacity, limited effectiveness in killing microorganisms (particularly, cyst-forming protozoa and viruses), adverse food effects (e.g., negatively affecting food flavor or appearance), inefficient energy conversion (electrical to light) and economic disadvantages.

In the area of water decontamination in particular, heretofore known methods of killing cyst-forming protozoa are in many cases ineffective and inefficient, i.e., overly time consuming or too costly. One commonly used method of water decontamination is the addition of chlorine to water for the purpose of killing microorganisms. Unfortunately, chlorine, at levels that are not also toxic to humans, is ineffective at killing some cyst-forming protozoans. In recent years, for example, outbreaks of *Cryptosporidium parvum* (*C.parvum*) have caused illness in hundreds of thousands of people, and have killed numerous others. Such outbreaks are common in the spring and summer rainy seasons when water from feedlots and the like may be undesirably mixed with municipal water supplies. No cost effective method of eradicating *C.parvum* has heretofore been available.

One attempt to eliminate live *C.parvum* from water involves exposing contaminated water to ultraviolet light. While limited success has been observed using ultraviolet light and special methods for increasing exposure time or intensity (such as by trapping oocysts in a mechanical filter and exposing the mechanical filter to ultraviolet light) to eradicate low concentrations of *C.parvum*, i.e., about 2 log cycle reductions, such method requires that the water be exposed to ultraviolet light having an intensity of 15 W/s for more than two hours, i.e., about 150 minutes. Thus, the use of ultraviolet light has proven not to be a viable approach to eradicating *C.parvum* in municipal water treatment facilities. What is needed is a method of eradicating *C.parvum*, other cyst-forming protozoa, and other microorganisms, such as viruses, that is both fast, i.e., that can be used practically in a water treatment facility, and that is highly effective, i.e., is effective to deactivate high levels of *C.parvum*, i.e., more than 2 or 3 log cycles.

In the area of air decontamination, airborne microorganisms, and in particular viruses, and even chemical contaminants, are of major concern. In order to be effective, an air treatment approach must be able to process flowing air as it passes from a contaminated space into an uncontaminated or sterile space. Heretofore, the most common method of air treatment has been to employ micro filters, such as HEPA filters, in a duct in order to physically remove particulate contaminants from the flowing air. Unfortunately, the micro filters employed pose significant impediment to air flow, and therefore require the use of high powered fans and the like in order to pump the air through the air filters. As more particulate contaminants become trapped in the micro filters over time, this impediment to air flow increases. In addition, due to the relatively high resistance to air flow posed by such microfilters, leakage of air around the filters becomes a significant factor in their design. Such filters also are subject to releasing trapped contaminants into the duct when they are removed for replacement and such released contaminants can be subsequently carried by the duct into areas sought to be protected by the filter. Furthermore, some microfilters may be unable to remove particularly small contaminant particles.

SUMMARY OF THE INVENTION

The present invention advantageously addresses the needs above as well as other needs by providing a method for deactivating cyst-forming protozoa, such as Cryptosporidium parvum, and viruses, such as poliovirus, using short duration pulses of very intense polychromatic light. Application of short duration pulses of high intensity, incoherent polychromatic light provides efficient, effective, high throughput processing and results in many practical and economic advantages.

Generally, in accordance with the present invention, methods are provided for deactivating microorganisms, including cyst-forming protozoa and viruses, by exposing the microorganisms to at least one short duration pulse of incoherent polychromatic light having an energy density in the range of from about 0.01 to about 50 joules per square centimeter using a wavelength distribution such that at least about 50%, and preferably at least about 70% or even 95% of its electromagnetic energy is distributed in a wavelength range of from 170 nanometers to 2600 nanometers, and a duration in the range of from about $1\times10^{-6}$ to about $1\times10^{-1}$ seconds, but preferably less than about 10 milliseconds.

Desirably, at least about 40 percent, and typically greater than about 70 percent of the energy of the light pulses should be of continuous emission spectra. However, intense pulses from sources including significant line emission spectra may also be beneficially utilized in specific processes. Such short, intense, incoherent light pulses may be provided by pulsed, gas-filled flashlamps, spark-gap discharge apparatuses, or other pulsed incoherent light sources.

Pulsed, gas-filled flashlamps produce broadband light when an electrical current pulse is discharged through the flashlamp, ionizing the gas and producing an intense burst of both continuum and line emission over a broad spectral range. Such flashlamps typically employ inert gases such as Xenon or Krypton because of their high efficiencies of electrical to optical energy conversion. The use of other gases or gas mixtures and gas discharge systems is possible and may be desirable for specific applications.

Desirably, the intensity of a particular wavelength distribution will be selected to provide at least a reduction of initially present colony forming units at the surface, or throughout the volume of a fluid media to be treated, by a factor of at least 10 (one log reduction, base 10) and more preferably at least one thousand (3 log cycles reduction, base 10) upon treatment with the intense pulses of light. Reduction of colony forming units by a factor of at least a million or more (6 log cycles reduction, base 10), ranging up to complete sterilization may be provided in accordance with the present invention.

In addition to solid food products that may exhibit dramatic improvements in shelf life and stability as a result of enzymatic and microbial inactivation, aseptic packaging materials, fluids such as air or water, and medical supplies such as surgical instruments, may also be subjected to intense, short pulses of polychromatic incoherent light. In accordance with such methods, at least about 5 percent, and preferably at least about 10 percent of the energy of the light pulses will be at wavelengths shorter than 300 nanometers. Such pulses may typically have relatively low total energy density, such as in the range of from about 0.01 to about 15 joules per square centimeter, and typically from about 0.1 to about 3 joules per square centimeter. A single pulse of such light having a broad spectral range may produce effective sterilization of a desired substrate, and may be absorbed by and damage with lethal effect a broad range of different groups of microorganisms. In accordance with various methods within the scope of the present invention, food products, fluids, such as water, juices or air, or packaging material, may be treated with intense, polychromatic incoherent light pulses having at least about 90 percent of their energy distributed between 170 and 2600 nanometers and a flash duration in the range of from about 0.001 and about 100 milliseconds at an energy density at the food or packaging material surface, or throughout the volume undergoing treatment in the range of from about 0.01 and about 20 joules per square centimeter. In addition to flashlamps, other pulsed light discharge devices producing appropriate broadband spectra and intensities may be used for the processes described herein.

Typically, food surfaces, fluids, and packaging substrates may be exposed to between about 1 and about 20 pulses of high intensity, short duration, incoherent light, with the use of a plurality of at least two pulses being particularly desirable. In various embodiments, the foodstuffs or fluids may be contained in a packaging material that is sufficiently transparent to the desired treatment spectrum prior to exposing its surfaces to the light pulses. In this regard, the packaging material containing the foodstuff, juice, water or other products to be treated may best transmit at least about 1% or more, preferably at least about 50%, of the energy of the light pulse over a predetermined treatment wavelength range less than about 320 nanometers.

In the treatment of fluids (such as air or aqueous liquids such as beverages, or water) which may contain undesirable microorganisms, intense incoherent polychromatic light pulses may be provided which have a specified energy density (as described herein) throughout the fluid volume undergoing treatment in a treatment zone. In this regard, at least a specified minimum energy level of the pulsed light should best be present throughout the treatment volume which is sufficient to produce the desired level of disinfection. Such methods may be static in a fixed treatment volume of fluid, or may, preferably, be continuous in which case the fluid is conducted through a treatment zone at a rate that (in conjunction with the light pulse rate, i.e., pulse repetition rate) assures that the entire volume of fluid passing through the treatment zone is subjected to the prescribed minimum level of pulsed light treatment, i.e., a prescribed minimum number of pulses. This later method is particularly suitable for use in applications such as in a municipal water treatment facility.

Various fluids such as substantially pure air and water have a high degree of transparency to a broad range of wavelengths, including the visible and ultraviolet spectral ranges, so that the treatment volumes and rates for such fluids may be relatively large. Other liquids such as clear sugar solutions, wine, etc. may have more limited transparency, which may be accommodated by the use of correspondingly smaller (e.g., thinner in the direction(s) of propagation of the light pulse) treatment volumes. It is preferred that the fluid have a transparency to light, such that at least half of incident light at 260 nanometers is transmitted through a 0.025 centimeter thickness of the fluid. Desirably, when treating fluid materials the fluids will be substantially free of solid, particulate materials (e.g., pure liquids or liquid mixtures, or solutions in which solids are dissolved in a liquid solvent) so that any microbial and/or enzymatic content of the fluid will be maximally subjected to the intense light field without shadowing effect. However, it will also be appreciated that solid materials such as cut, sliced or particulate foods (e.g., dried vegetables) may be conveniently treated in a fluid (e.g., water) suspension medium, preferably with multiple pulses, which may desirably be in multiple propagation directions to insure that all solid surfaces are treated.

In addition to treating fluids by providing a suitable intensity of pulsed incoherent light throughout the volume of fluid to be treated, the fluid may also be treated by providing multiple pulsed light treatment with mixing (preferably turbulent mixing) of the fluid between the individual pulses. However, while such treatment methods may reduce the microbial and/or degradative enzymatic content, they are significantly less desirable and less efficient than the whole volume treatment methods.

A plurality of the closely spaced pulses of intense light, and in some cases a single pulse, will substantially reduce the population of viable microorganisms, such as cyst-forming protozoa and viruses, typically by greater than about one order of magnitude (base 10) and preferably at least two or more orders of magnitude. Higher levels of reduction (including complete sterilization) may be accomplished at appropriate energy levels and treatment pulse numbers. Usually between about 1 and about 50 pulses of light are used to sufficiently treat a food, fluid, medical device or packaging material surface, and preferably between about 1 and about 20 pulses are used. Typically between 1 and 10 flashes are used, e.g., 2, 5 or 10 flashes. It is generally desirable that a plurality of at least 2 of the high intensity light pulses be applied.

The time between pulses applied to the surface being treated desirably be generally between 0.001 seconds and about 30 seconds (e.g., 0.1 to 5 seconds), and preferably less than about 2 seconds in commercial treatment applications. When the pulses are provided by a single flashlamp (or flashlamp assembly of a plurality of lamps that are flashed simultaneously), the maximum repetition rate is governed as a practical matter by individual lamp cooling parameters, which will typically provide a repetition rate in the range of from about less than 1 to about 1000 times per second. However, the effective repetition rate may be increased by employing multiple flashlamps which are sequentially flashed either individually or in groups such as pairs, and by providing relative movement between the flashlamp and the surface or volume being treated.

Incoherent pulsed light of sufficient intensity as well as appropriate duration and wavelength distribution is obtainable from a flashlamp system. A suitable flashlamp system is sold by PurePulse Technologies, Inc., under the trademark PUREBRIGHT. A particular model, the PUREBRIGHT Model PBS1-3, consists of a DC power supply, which charges energy storage capacitors, a switch used to control the discharge of these capacitors, a trigger circuit to fire the switch at pre-programmed time intervals (automatic mode) or when a button is depressed by the operator (manual mode), a set of high voltage coaxial cables carrying the discharge pulses from the capacitor-switch assembly, and from one to four flashlamps mounted in reflectors to direct the light emitted from the lamps.

In one embodiment, the present invention can be characterized as a method of deactivating cyst-forming protozoa, viruses or the like. The method involves illuminating the cyst-forming protozoa, viruses or the like using at least one short duration, high intensity pulse of broad spectrum polychromatic light. In variations of this embodiment, the light has an intensity of at least 0.1 J/cm$^2$, e.g., of from between about 0.5 and 1.5 J/cm2, the pulse duration is from between about 10 nanoseconds and 10 milliseconds, and/or at least 50% of the pulse's energy is transmitted in light having wavelength from between about 170 and 2600 nm.

Advantageously, the cyst-forming protozoa may be *Cryptosporidium parvum*, which is unaffected by conventional water treatments, such as chlorine, and against which continuous ultraviolet light has proven of little or no effect. The viruses may be poliovirus, rotavirus or other viral agents.

In another embodiment, the present invention can be characterized as method of decontaminating water or air containing microorganisms. The method involves illuminating the water or air using at least one short duration, high intensity pulse of broad spectrum polychromatic light. In variations of this embodiment the light has an intensity of at least 0.1 J/cm$^2$, e.g., from between about 0.5 and 1.5 J/cm$^2$; the pulse duration is from between about 10 nanoseconds and 10 milliseconds; and/or at least 50% of the pulse's energy is transmitted in light having wavelengths from between about 170 and 2600 nm.

Advantageously, the water may contain *Cryptosporidium parvum* oocysts, viruses or other microorganisms, and such method is effective to deactivate these *Cryptosporidium parvum* oocysts, viruses, and other microorganisms. The air may contain such microorganisms and such method is effective to deactivate these microorganisms in air as well.

In operation, the water or air may be flowed into a treatment zone, and the illuminating may take place in the treatment zone. After the water or air is illuminated in the treatment zone, the water or air is flowed out of the treatment zone. The flowing of the water or air may be accomplished by containing the water or air in appropriate pipes, and by pumping the water or air into and/or out of the treatment zone. The flowing of the water or air may be carried out continuously with the illuminating being repeated at a flash repetition rate selected so that all of the water or air passing through the treatment zone is illuminated before it exits the treatment zone.

Advantageously, an outlet port of the treatment zone may be positioned to receive high-intensity, short-duration pulses of polychromatic light in a broad spectrum so as to deactivate microorganisms present in the outlet port that may otherwise contaminate decontaminated water leaving the treatment zone.

It is therefore a feature of the invention, in some embodiments and variations, to deactivate cyst-forming protozoa, viruses and other microorganisms.

It is another feature of the invention, in some embodiments and variations, to deactivate such microorganisms using short-duration, high-intensity pulses of broad-spectrum polychromatic light.

It is a further feature of the invention, in some embodiments and variations, to deactivate cyst-forming protozoa, viruses and other microorganisms in fluids, and water and air in particular.

It is an additional feature of the invention, in some embodiments and variations, to deactivate cyst-forming protozoa, viruses and other microorganisms in fluids as such fluids are passed through a treatment zone.

It is an added feature of the invention, in some embodiments and variations, to deactivate cyst-forming protozoa using pulses that have a prescribed pulse repetition rate such that all fluid passing through a treatment zone is treated with at least one intense, short duration pulse of broad spectrum, polychromatic light.

BRIEF DESCRIPTION OF THE DRAWINGS

The above and other aspects, features and advantages of the present invention will be more apparent from the following more particular description thereof, presented in conjunction with the following drawings wherein.

Figure 1:
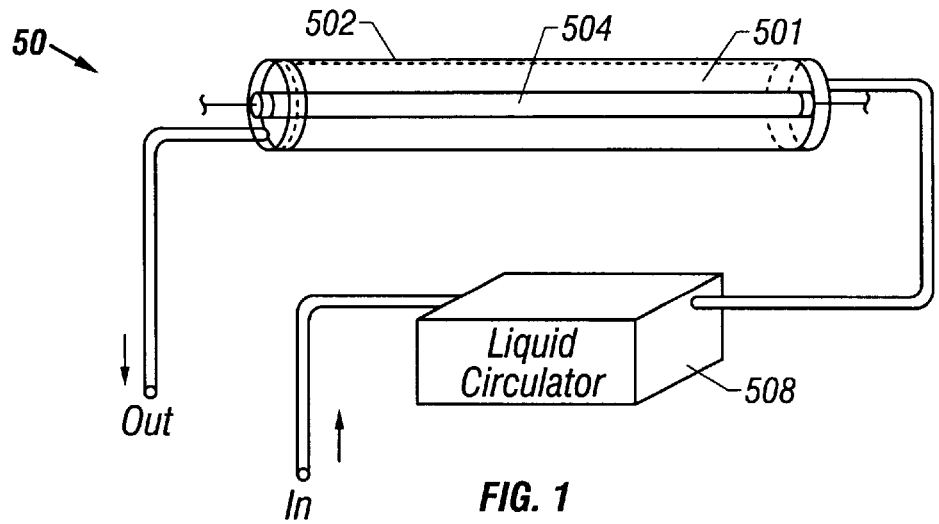
FIG. 1 is a schematic view of an embodiment of a pulsed light processing apparatus that treats pumpable products, such as water or air, flowing longitudinally through a jacket surrounding an elongated, incoherent pulsed light source.

The APPENDIX is a collection of test results obtained in accordance with the procedures set forth below in EXAMPLE I.

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Referring to FIG. 1, a flashlamp system that may, for example be a flashlamp system, such as PUREBRIGHT Model No. PL-320 available from PurePulse Technologies, Inc. of San Diego, Calif., includes a pulsing device (not shown) that includes a DC power supply that charges energy storage capacitors (not shown); a switch (not shown) used to discharge the capacitors; a trigger circuit (not shown) used to fire the switch at pre-programmed time intervals in response to sensors that detect a liquid flow rate or the like, or in response to a button being depressed; and a set of high voltage coaxial cables (not shown) carrying the discharge pulses from a capacitor-switch assembly to a flashlamp assembly. The flashlamp assembly includes from one to four or more flashlamps 504 mounted in metal reflector assembly 502 so as to direct polychromatic light emitted from the flashlamps 504 toward the fluid, e.g., water, liquid food product or air, flowing through a treatment conduit, thereby exposing the fluid to such light.

Such exposure deactivates, i.e., kills or sterilizes, substantially all (i.e., more than 50%, e.g., 90%) of the microorganisms in the fluid flowing in the treatments conduit.

The intense (i.e., 0.01 to 50 J/cm$^2$, e.g., between 0.5 and 1.5 J/cm$^2$, energy density measured at the surface of the metal reflectors 502), short duration pulses of polychromatic light in a broad spectrum (i.e., 170 to 2600 nm; $1.8 \times 10^{15}$ Hz to $1.2 \times 10^{14}$ Hz) are preferably from between 0.001 $\mu$s to 100 ms, e.g., between 10 nanoseconds to 10 milliseconds, in duration and have a pulse repetition rate of from one to 100 pulses, e.g., 10 pulses, per second.

Note that the light may also include continuous wave and monochromatic or polychromatic light having wavelengths outside the broad spectrum. However, at least 50% to 60%, preferably at least 70% to 90% or more, of the energy of the light should be from light having wavelengths within the broad spectrum defined above.

FIG. 1 is a schematic view of an embodiment for the treatment of pumpable products such as air, water or liquid food products, such as fruit juices with pulses of intense incoherent pulsed light. The apparatus 50 comprises a reflective, cylindrical enclosure defining a treatment cavity 501 through which the fluid flows and that surrounds a pulsed light source 504, which in the apparatus 50 shown may be a high intensity Xenon flashlamp provided with a suitable power source (not shown) in accordance with conventional practice for flashlamp operation. The reflective treatment cavity 501 serves to increase the effective energy density of the pulses of light that impinge upon the volume of pumpable products passing therethrough. A circulation pump 508 controls the flow rate of the pumpable product through the treatment cavity 501, which is coordinated with the pulse repetition rate of the flashlamps so that during the product's residence time within the treatment cavity 501, all of the product that passes therethrough receives a predetermined number of high-intensity, short-duration pulses of incoherent, polychromatic light in a broad spectrum.

The product exiting the treatment cavity 501 will therefore be sterile or disinfected to the degree desired (as determined in accordance with the number of pulses of light and the energy density of the pulses of light throughout the treatment volume).

In some embodiments, the treatment cavity 501 is suitably arranged so as to be separated from the flashlamp 504 so as to prevent the product from contacting the flashlamp 504. The diameter of the treatment cavity 501 will vary depending upon many factors including but not limited to the specific light absorption characteristics of the product to be treated within the broad spectrum. The diameter of the treatment cavity 501 also varies as a function of the physical and operating characteristics of the flashlamps and the degree of product mixing expected between multiple pulses.

The treatment cavity 501 preferably includes the metal reflector assembly 502 as its outer wall or as an external reflector, in order to reflect illumination traversing the product back inward toward the flashlamp. It is noted that fluids such as air and water are relatively transparent to light. Accordingly, there is relatively little attenuation through absorption in such products, with the flux density decreasing largely only as a function of distance from the flashlamp. However, for fluids that have significant absorption, such as some liquid food products, such as juices, this factor will also decrease the flux density of the light emitted from the flashlamp as a function of distance from the flashlamp. In any event, the desired minimum flux density, as previously described, preferably should be maintained throughout the treatment zone or alternatively mixing must occur to insure that all of the fluid is subjected to the appropriate minimum flux density and number of pulses.

Figure 2:
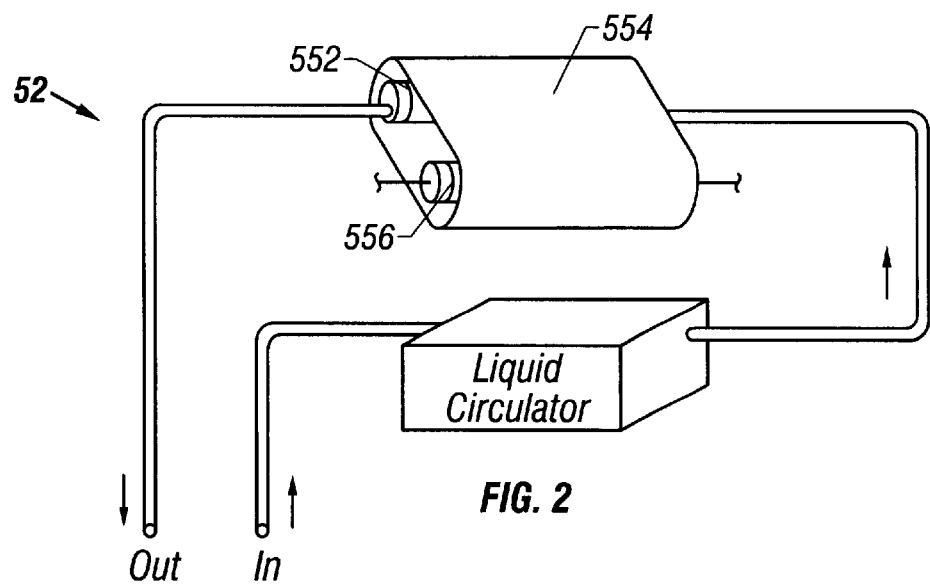
FIG. 2 is a schematic view of another embodiment of the pulsed light processing apparatus of FIG. 1 that treats pumpable fluids, such as water or air, flowing in a direction parallel to one or more elongated incoherent light sources.

Referring to FIG. 2, while the flashlamp 556 is located internally of the treatment chamber 501 in the apparatus 50, (FIG. 1) one or more lamps may also or alternatively be located externally of the treatment chamber 501 in an alternative apparatus 52. An alternative design, as shown in FIG. 2, in which the fluid, e.g., liquid food product, water, or air, to be treated is conducted through a transparent treatment conduit (e.g., a quartz glass tube) 552 that is positioned along one focus of an elliptical reflector 554. A flashlamp 556 is positioned along another focus of the elliptical reflector 554. Multiple elliptical segments (not shown), each having a lamp at one focus and the quartz tube 552 at the other focus, may be utilized if desired. In this manner, because the light emitted from the flashlamp 556 is focused toward the center of the treatment chamber, compensation is provided for the light absorption of the liquid being treated, so that all of the liquid is subjected to more uniform light treatment.

The flashlamp 556 may be jacketed in, e.g., a quartz sleeve or jacket for water or air cooling and/or spectral filtering (as can the flashlamp 504 in FIG. 1).

Figure 3:
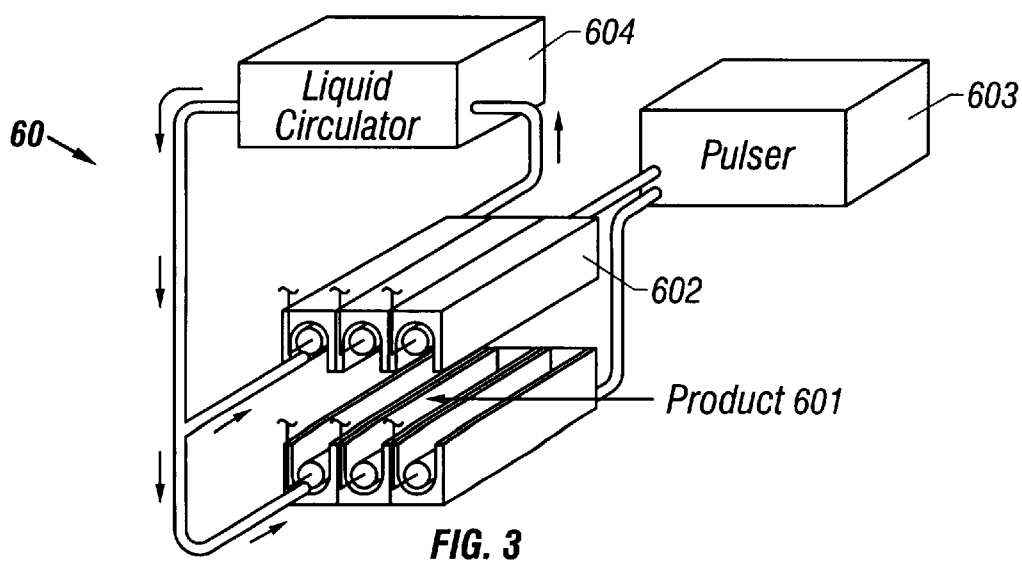
FIG. 3 is a schematic view of an embodiment of a processing apparatus for treating products passing through an intense incoherent pulsed light treatment station.

Referring to FIG. 3, an embodiment is shown of an intense incoherent light processing station 60 having a pulsed light source/reflector array 602 through which the product 601 passes, for example, in quartz tubing (not shown). The flashlamp/reflector array 602 is connected by umbilicals to an electrical pulse forming network 603 or pulser that energizes the flashlamp array either simultaneously or sequentially and a cooling/filtering circulation pump 604 that circulates liquid medium through a jacket assembly external to each lamp for cooling and/or spectral filtering by the use of selected solutions with the desired spectral transmittance/absorbance characteristics. For high speed operation and high power densities, it may be desirable to cool the flashlamps using an optional quartz containing water jacket.

The flashlamp/reflector array 602 comprises a plurality of lamps and reflectors that create intense, short-duration light pulses in a treatment region between upper and lower halves of the flashlamp/reflector array 602. While the illustrated processing station 60 uses straight lamps and reflector elements, other arrangements may be utilized. For example, flashlamps may be constructed in any shape in much the same way that neon lighting signs may also be made to any shape. Similarly, the reflector elements may be made of many different materials in many different geometries to accommodate imaging the flashlamp source upon the treated product with a desired energy density distribution. "The Optical Design of Reflectors", Second Edition, William B. Elmer, Published by John Wiley and Sons, Inc., New York is an appropriate resource as an introduction to the fundamentals of reflector design.

Although the present invention includes many potential applications for the reduction of viable organisms, microbe or virus numbers or enzymatic activity in the preservation of food products, the use of high intensity, short time duration light treatment for the sterilization of water in water treatment applications and air in air treatment applications is considered an important aspect of the present patent document. For example, even at very high organism densities (up to $1 \times 10^6$/ml to $1 \times 10^7$/ml *Cryptosporidium parvum* oocysts M1), only two flashes at an energy density of 1 J/cm² per flash will result in sterilization of the *Cryptosporidium parvum*.

Referring to FIG. 4, a cross-sectional view is shown of a water treatment cell 700 in accordance with one embodiment of the present invention. Shown are an outer cylindrical housing 702, a cylindrical baffle 704, a first end plate 706 and a first lamp holder 708, a second end plate 710 and a second lamp holder 712, a water inlet 714, and first and second water outlets 716, 718. Located coaxially with the outer cylindrical housing 702 and cylindrical baffle 704 is a flashlamp 722 of the type described hereinabove.

The outer cylindrical housing 702, along with the first and second end plates 706, 710 form a water-tight container into which water flows through the water inlet 714, and out of which water flows through the first and second water outlets 716, 718. Coaxial with the outer cylindrical housing 702 is the cylindrical baffle 704. The cylindrical baffle 704 is mounted to the second end plate 710 and terminates just short of the first end plate 706 such that water can flow from a region within the water-tight container outside the cylindrical baffle 704, around an end 720 of the cylindrical baffle 704 near the first end plate 706 and into a region within the cylindrical baffle 704.

This arrangement provides for a fluid flow pattern that is as follows: water flows into the water-tight container through the water inlet 714 and into the region outside the cylindrical baffle 704; next the water flows past the cylindrical baffle 704 (to the left as oriented in FIG. 4) and around the end 720 of the cylindrical baffle 704; the water next flows within the cylindrical baffle 704 back toward the second end plate (toward the right as oriented in FIG. 4) and exits the cylindrical housing through the water outlets 716, 718.

Advantageously, the above-described configuration provides for a substantially uniform eddy-free flow of water in the region within the cylindrical baffle 704. This is largely due to flow uniformities achieved when the water flows over the end 720 of the cylindrical baffle 704 into the region within the cylindrical baffle. As a result, uniform treatment with the high-intensity, short-duration pulses of light in a broad spectrum is achieved. The creation of a uniform flow dynamic in the region within the cylindrical baffle 704 is further achieved by the use of an annular baffle 725 positioned between the cylindrical baffle 704 and the outer cylindrical housing 702 about 5 centimeters in from the inlet port 714. This annular baffle 726 helps to distribute the water flowing in through the inlet port 714 throughout the region between the cylindrical baffle 704 and the outer cylindrical housing 702.

During its residency within the cylindrical baffle 704, the water is exposed to high intensity, short-duration pulses of polychromatic light emitted from the flashlamp 722. Advantageously, the inner surface 724 of the cylindrical baffle 704 is reflectorized such that light emitted from the flashlamp 722 and passing through the water in the region within the cylindrical baffle 704 is reflected back toward the flashlamp 722. The reflected light is therefore passed back through the water, thereby increasing the effective energy density to which the water in the region within the cylindrical baffle 704 is exposed. This effective energy density is increased even further in view of the fact that the light is preferably reflected back and forth multiple times within the region within the cylindrical baffle 704 before being absorbed by microorganisms and other particles within the water, by the reflectorized inner surface of the cylindrical baffle 704, etc.

Preferably, the energy density to which the water within the cylindrical baffle is exposed is from between 0.01 J/cm$^2$ and 50 J/cm$^2$, e.g., between 0.5 J/cm$^2$ and 1.5 J/cm$^2$. The pulse duration of the high-intensity, short-duration pulses of polychromatic light is from between 0.001 $\mu$s and 100 ms, e.g. between 10 nanoseconds and 10 milliseconds, and the pulse repetition rate is from between 1 Hz and 100 Hz for a cylindrical baffle having a length of from between 50 millimeters and 500 millimeters, e.g., 220 millimeters and a diameter from between 25 millimeters and 250 millimeters, e.g., 114 millimeters. Preferably, the flashlamp emits at least 50% to 60%, e.g., 70% to 90% of its light at wavelengths of from between 170 nm and 2600 nm. Furthermore, preferably at least from between 1% and 1%, e.g., 10% of the energy density of the light emitted from the flashlamp is concentrated at wavelengths of from between 200 nanometers and 320 nanometers, e.g., 260 nanometers.

Figure 5:
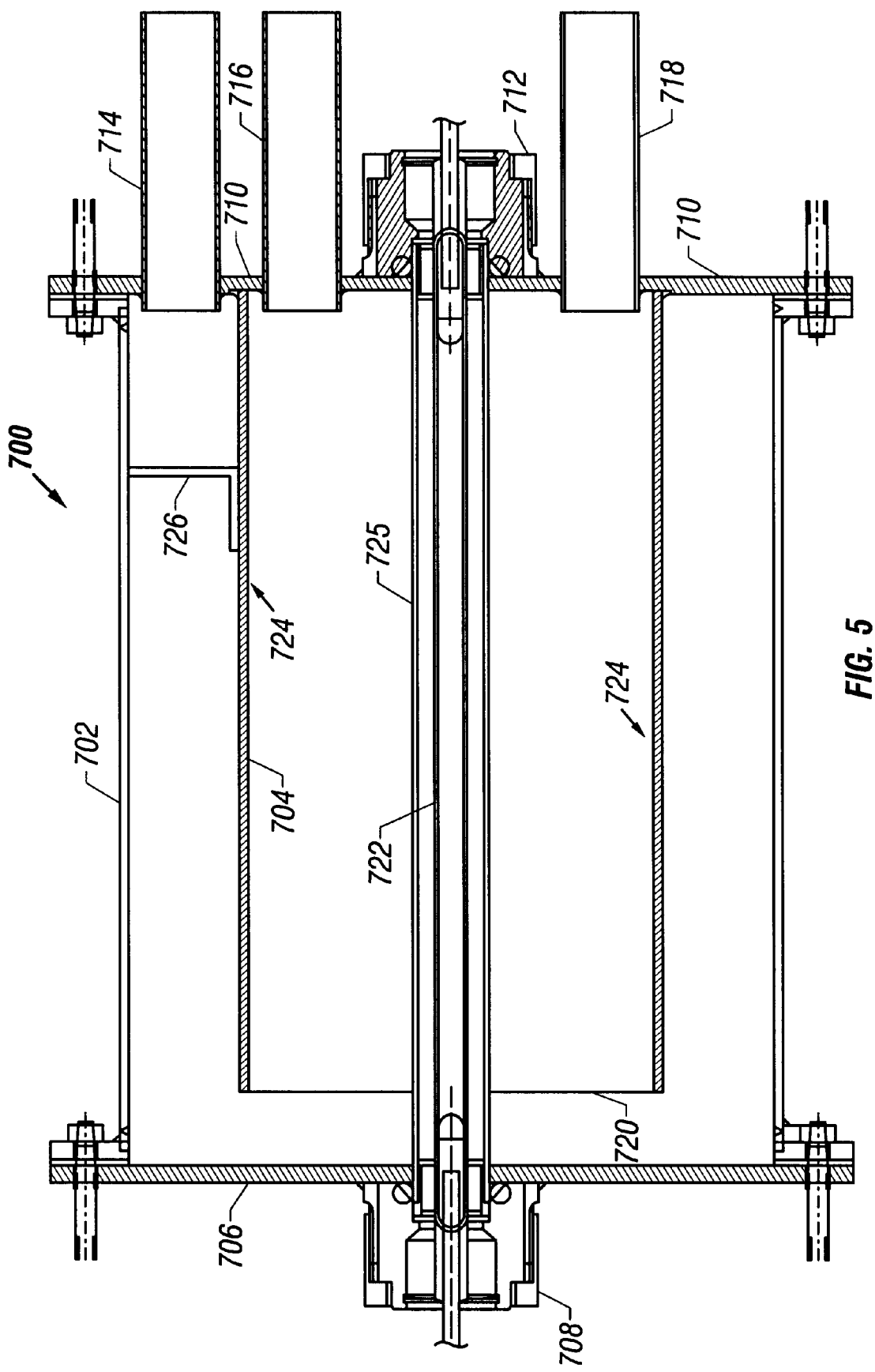
FIG. 5 is a cross-sectional view of another embodiment of the pulsed light processing apparatus of FIG. 4, wherein a quartz jacket is employed surrounding the elongated, incoherent pulsed light source and through which air or water is flowed in order to cool the elongated, incoherent pulsed light source.

Referring to FIG. 5, a cross-sectional view is shown of a water treatment system or cell 700 made in accordance with another embodiment of the present invention. Shown are the outer cylindrical housing 702, the first and second end plates 706, 710 and lamp holders 708, 712, the water inlet 714, the first and second water outlets 716, 718, the cylindrical baffle 704, the flashlamp 722, and a quartz jacket 725.

Except as described hereinbelow, the embodiment of FIG. 5 is substantially the same as the embodiment of FIG. 4

The quartz jacket 725 provides a water tight barrier that separates space within the cylindrical baffle 704 from a space immediately proximate to the flashlamp 722. This arrangement allows air or cooling water to be circulated within the space immediately proximate to the flashlamp 722 for the purpose of cooling the flashlamp 722 or for spectrally filtering the light emitted from the flashlamp 722. Advantageously, the embodiment of FIG. 5 may provide for longer flashlamp life, a more desirable frequency spectra, and/or a shortened pulse repetition rate (due to increased flashlamp cooling between flashes) than possible in the embodiment of FIG. 4.

Figure 6:
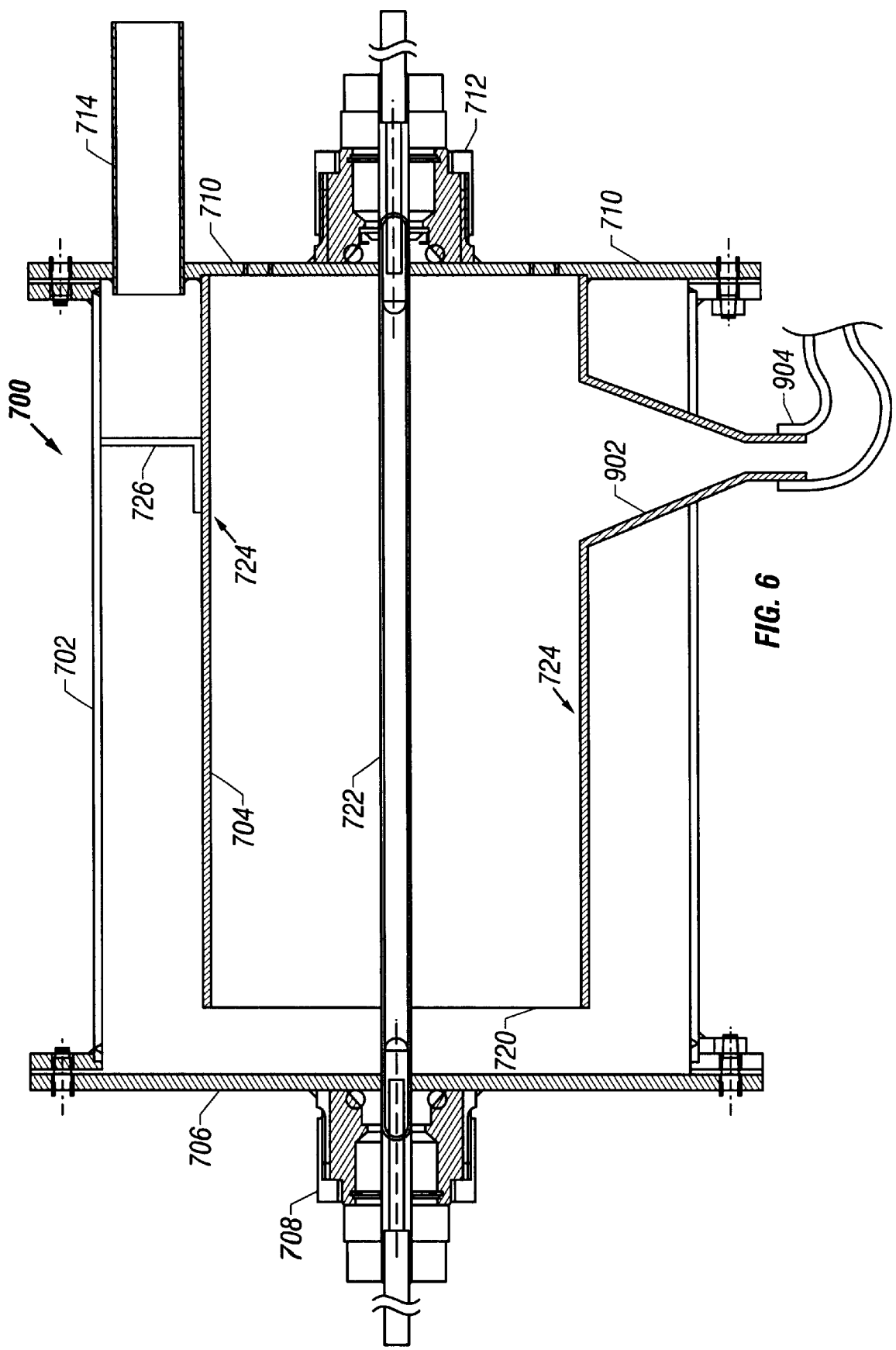
FIG. 6 is a cross-sectional view of a further embodiment of the pulsed light processing apparatus of FIG. 4, wherein an outlet port is positioned to receive high-intensity, short duration pulses of polychromatic light in a broad spectrum emitted from a flashlamp.

Referring to FIG. 6, a cross-sectional view is shown of a water treatment system 700 made in accordance with another embodiment of the present invention. Shown are the outer cylindrical housing 702, the first and second end plates 706, 710 and lamp holders 708, 712, the water inlet 714, the cylindrical baffle 704, the flashlamp 722, and a annular baffle 726.

Except as described hereinbelow, the embodiment of FIG. 6 is substantially the same as the embodiment of FIG. 5.

Figure 4:
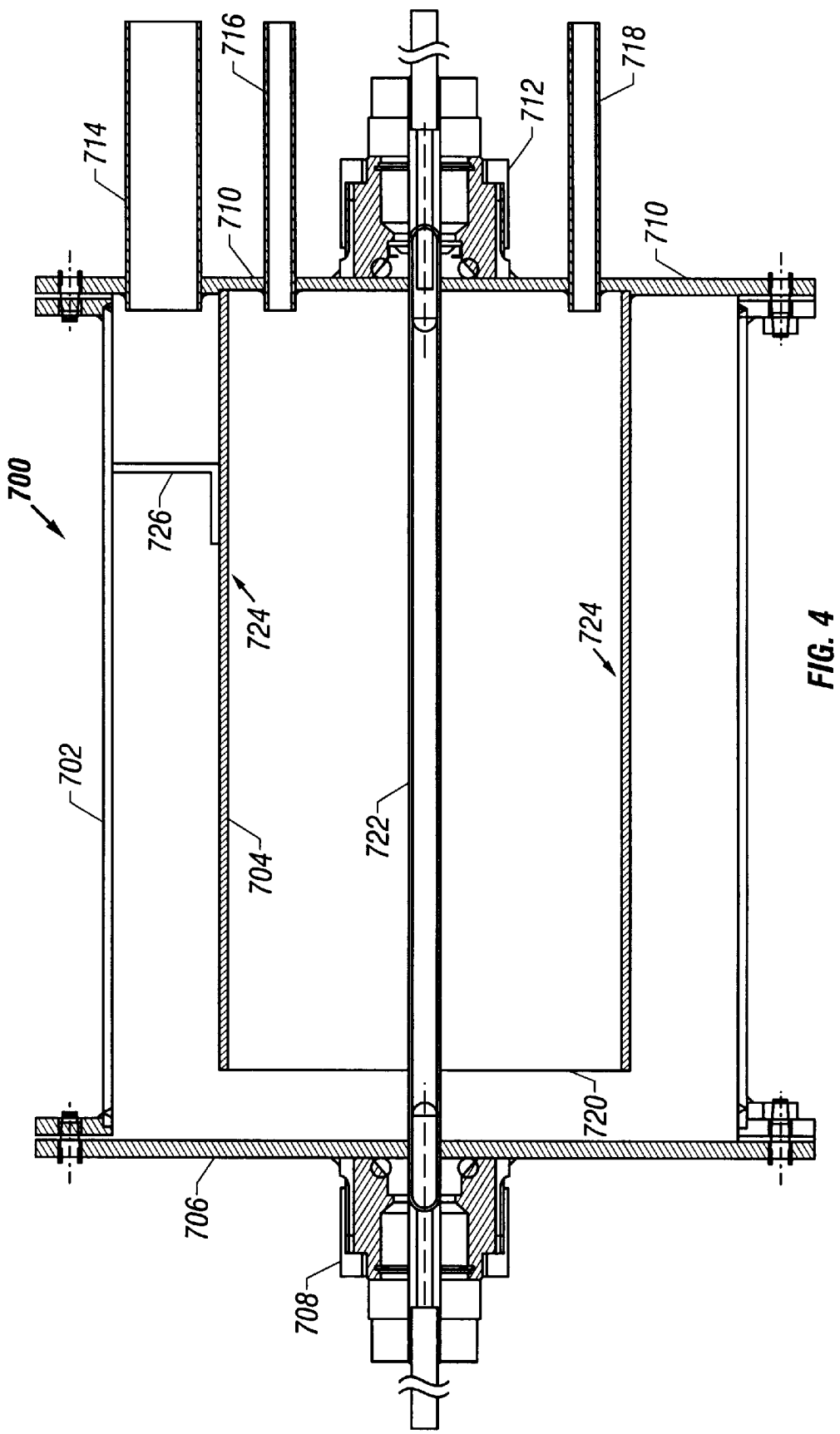
FIG. 4 is a cross-sectional view of an embodiment of a processing apparatus for treating water flowing through a treatment chamber made up of two concentric cylindrical structures in which an elongated, incoherent pulsed light source is positioned along a central axis.

The first and second water outlets 716, 718, of FIG. 4 are replaced in the embodiment of FIG. 6 with a single frusto-conical outlet 902 that passes through the side of the cylindrical baffle 704 thereby permitting light from the flashlamp 722 to irradiate the interior of the frustoconical outlet 902.

This arrangement prevents contaminants from surviving within the frustoconical outlet 902 and contaminating decontaminated water as it exits the treatment system 700. A recirculating hose 904 receives water from the frustoconical outlet 902 when decontaminated water or air is not needed, and recycles such water through the water treatment system 900. When the recirculating hose 904 is removed, decontaminated water flows through the frustoconical outlet and can be utilized as needed.

This embodiment is particularly suited for laboratory use where water is withdrawn from the water treatment system 700 periodically, and contamination of the water after it exits the water treatment system 700 is of particular concern. Numerous uses of the present embodiment are however contemplated.

Figure 7:
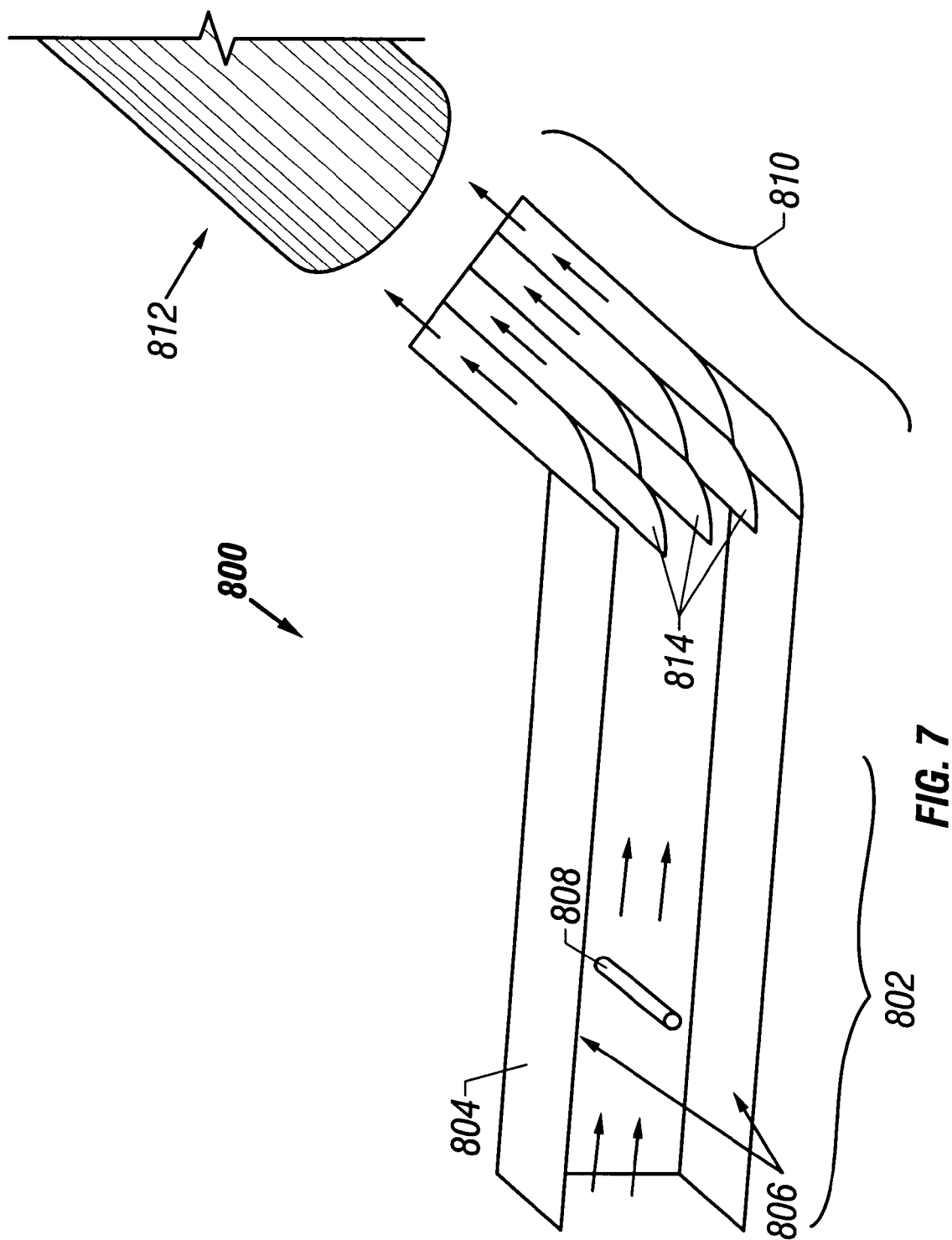
FIG. 7 is a perspective view of a pulsed light processing apparatus that treats air flowing through a duct in which an elongated, incoherent pulsed light source is positioned transverse to the airflow.

Referring next to FIG. 7, a perspective view is shown of an air treatment system 800 in accordance with one embodiment of the present invention. Shown are a treatment region 802 of an air duct 804, including a reflective inner surface 806, a transversely oriented flashlamp 808, a baffled exit region 810 of the air duct 804 and an exhaust duct 812.

In operation, air is flowed into the treatment region 802 of the air duct 804, as a result of a vacuum pressure created by a fan (not shown) in the exhaust duct 812. The air is flowed within the treatment region 802 of the air duct 804 past the flashlamp 808. During its residence within the treatment region 802, the air is exposed to one or more high-intensity, short-duration pulses of polychromatic light in a broad spectrum, which are emitted from the flashlamp 808. Advantageously, the effective energy density to which such air is exposed during its residency within the treatment region 802 is dramatically increased by the presence of a reflectorized interior surface of the treatment region 802, which causes light emitted from the flashlamp 808, and passing through air within the treatment region, to be reflected back into the air within the treatment region.

After passing through the treatment region 802, the air passes into baffles 814 in the exit region 810. The exit region 810 contains, for example, three baffles 814 that separate the exit region 810 into four distinct airways. The baffles 814 help to assure uniform air flow as the air exits the air duct 804, and more importantly, serve to prevent light emitted from the flashlamp 808 from exiting the treatment region 802. In order to further prevent light from exiting the treatment region 802, an interior surface of each of the four distinct airways is painted flat black.

If desired, an entrance region through which the air flows before reaching the treatment region 802 may also contain baffles like those in the exit region 810, and such baffles can be painted flat black. The baffles at the entrance region (not shown) also, like the baffles at the exit region 810, prevent light emitted from the flashlamp 808 from exiting the treatment region.

After exiting the air duct 804 through the exit region 810, treated air is sucked into the exhaust duct 812 where it is directed to a space in which sterile air is desired. The exhaust duct 812 is suitably connected to the air duct 804 so as to prevent untreated air from entering the exhaust duct 812.

Having generally described the present invention, various aspects of the invention will now be described in greater detail by way of the following specific examples. These examples demonstrate qualitatively and quantitatively the effectiveness of the invention for decontamination of fluids, specifically water, and air by reducing or eliminating microorganisms, specifically cyst-forming protozoa and viruses, more specifically *Cryptosporidium parvum* oocysts and poliovirus, and the like.

EXAMPLE I

Five vials containing 1 ml each of $1\times10^7$/ml suspension of *Cryptosporidium parvum* oocysts and five vials containing 1 ml each of $1\times10^6$/ml suspension of *Cryptosporidium parvum* oocysts are obtained. Four vials of each oocyst concentration are processed as follows. One vial at each concentration is exposed to each of the following amounts of pulsed very-high-intensity, broad-spectrum polychromatic light: 0 flashes, 2 flashes, 5 flashes, and 10 flashes, all at 1 Joule/$cm^2$. Approximately 800 microliters of each original (1000 microliters) suspension is recovered and transferred to fresh vials (labeled, siliconized microfuge tubes). Each oocyst preparation is condensed by centrifugation to approximately 200 microliters and administered to neonatal mice in 25 microliter volumes. After approximately one week (6½ days) the mice are euthanized by carbon dioxide inhalation. A terminal colon (approximately 1 cm) is removed from each neonatal mouse and placed in a microfuge tube containing 400 microliters of 2.5% potassium dichromate (w/v in deionized water). A remaining portion of the intestinal tract is removed from each of the neonatal mice and pooled with the intestinal tracts from the other neonatal mice within respective treatment groups (according to the number of flashes of light administered to each sample). The terminal colon samples are vortexed vigorously and the supernatants are processed over discontinuous sucrose gradients to recover and isolate oocysts. The samples are incubated with a Cryptosporidium oocyst specific monoclonal antibody conjugated with fluorescein isothiocyanate (OW 50-FITC) and is analyzed by flow cytometry.

Logical gating identifies the oocysts that are enumerated in 100 microliters of each sample suspension. This volume represents approximately $1/12$ of the original sample volume. The raw data (number of events in the logical gate representing oocysts) for each sample along with example flow cytometry plots for positive and negative samples are included in the APPENDIX, on pages 3–4 and 1–2 respectively. A three dimensional bar chart, also included in the APPENDIX, on page 5, illustrates the mean oocyst number for each treatment group (and an uninfected control group).

The pooled intestines from each group are homogenized in potassium dichromate and the homogenate is evaluated in a manner similar to that described above for the terminal colon segments. The purpose of the pooled intestine assay is to attempt to detect low numbers of oocysts in the pooled samples that may have been missed in individual terminal colon samples. The oocyst numbers are presented for these samples in the APPENDIX on page 6.

As can be seen based on the information presented in the APPENDIX, no evidence of infection is observed in the intestinal samples from mice inoculated with oocysts that received any tested level of treatment of pulsed, high-intensity, broadband, polychromatic light, while mice receiving control oocysts exhibited large numbers of oocysts in their intestinal samples.

These tests show that even high C.parvum oocysts concentrations can be rendered non-infectious as measured by in vivo infectivity assays.

EXAMPLE II

Using a 100 microliter pipettor, from 700 microliters of a solution containing approximately $25\times10^6$ Cryptosporidium oocysts approximately 200 milliliters of solution is transferred into a 1 millimeters thick space between two quartz discs. The disks are gently tilted until the Cryptosporidium-oocyst-containing solution is positioned in the center of the disks. The disks are positioned on a lab jack so that the Cryptosporidium-oocyst-containing solution is centered under a flashlamp set to deliver 0.1 Joules/$cm^2$ energy density measured at the Cryptosporidium-oocyst-containing solution. A number of flashes are emitted from the flashlamp at a pulse duration of 300 microseconds and a pulse repetition rate of 1 flash per second. The Cryptosporidium-oocyst-containing solution is then withdrawn from between the quartz disks using a sterile pipettor and is placed in a sterile labeled vial. Control suspensions were also prepared by transferring the Cryptosporidium-oocyst-containing solution to the quartz disks, and then moving them into the vial without treatment using pulsed light.

The control suspensions are prepared for dilution yielding $10^6$, $10^5$, and $10^4$ *Cryptosporidium parvum* oocysts per milliliter, e.g, a 50 microliter aliquot of the control suspension is diluted in 450 microliters tissue culture grade phosphate buffered solution (T-PBS) yielding a 1/10 dilution. Control and treated *Cryptosporidium parvum* oocyst suspensions are titrated to suspend oocysts and are dispensed into four-day cultures of Maden-Darby Canine Kidney (MDCK) cells (in Ultraculture). Each oocyst suspension is dispensed in a 100 microliter volume in duplicate chambers (two per treatment). Remaining oocyst suspensions are stored at 4° centigrade. The four-day cultures are incubated at 37° centigrade (5% $CO_2$). Each chamber is washed at three hours PI with T-PBS and fresh culture medium is replaced. Fresh culture medium is again replaced at 24 hours PI. At 48 hours PI chambers are washed with T-PBS three times and fixed with Bouings solution for approximately one hour (2.0 milliliters per chamber well).

The Bouings solution is decolorized by five successive washings with 70% ethanol over the course of one hour. The chambers are washed with T-PBS and the T-PBS is replaced with phosphate buffered solution/bovine serum albumin (PBS/BSA) and incubated for 30 minutes. The PBS/BSA is replaced with fluorochrome-labeled monoclonal antibodies solution (C3C3-CyC, 1/500th dilution, 300 microliter per chamber). The chambers are then incubated for 90 minutes at room temperature in the dark on a rocker platform. The chambers are then washed three times with T-PBS. The T-PBS is aspirated and two drops of polyvinyl alcohol/anti-quenching agent (PVA II/DABCO) (the anti-quenching agent is 1,4-diazabicyclo-[2.2.2] octane from Sigma Chemical Company) is added to each chamber. Cover slips (18 square millimeters) are mounted taking care not to trap air bubbles therebeneath. Excess T-PBS or PCA II/DABCO is aspirated. Parasite development is then scored microscopically for each dilution and disinfectant treatment.

The control and treated oocyst preparations are titrated and dispensed into microcentrifuge tubes (100 microliters per tube). An equal volume of DMEM base medium supplemented with 1.5% NaT is added and the tubes are incubated at 37° centigrade for 45 minutes. Excystation is accessed by preparing wet mounts and scanning the slides for free sporozytes and empty and partially empty oocyst walls.

As can be seen based on the information presented in Table 1 below, in vitro culturization results show that all treatment levels except a single flash at 0.11 Joules/$cm^2$ effectively inactivated oocysts or reduced the infectivity to a level below approximately 100 oocysts, which is the limit of detection for the results presented.

TABLE 1

| Treatment (Joules) | Oocysts per Chamber | In vitro growth 1 Flash | | 2 Flash | |
|---|---|---|---|---|---|
| 0.11 | $10^6$ | <1 + | <1 + | — | — |
| 0.22 | $10^6$ | — | — | — | — |
| 0.44 | $10^6$ | — | — | — | — |
| 0.67 | $10^6$ | — | — | — | — |
| 0.89 | $10^6$ | — | — | — | — |
| 1.11 | $10^6$ | — | — | — | — |
| Control | $10^6$ | >4 + | >4 + | NA | NA |
| Control | $10^5$ | 3–4+ | 3–4+ | NA | NA |
| Control | $10^4$ | 2–3+ | 2–3+ | NA | NA |
| Control | $10^3$ | 1–2+ | 1–2+ | NA | NA |

These results indicate that oocyst infectivity was reduced by between 3 and 5 log cycles or greater at two flashes of 0.11 Joules/$cm^2$ or alternatively, one flash at 0.22 Joules/$cm^2$ minimum treatment. While at 0.11 Joules/$cm^2$ and 0.22 Joules/$cm^2$, one or two flash treatments, at least a few sporozytes are indicated with excysted oocysts, as indicated in Table 2 below, it appears based on the results presented that liberated sporozytes from two flash treatment at 0.11 Joules/$cm^2$ or greater renders the oocytes incapable of infecting and/or growing in host cell monolayers.

TABLE 2

| Treatment (joules) | Oocysts per Chamber | Excystation (with sporozites) 1 Flash | 2 Flash |
|---|---|---|---|
| 0.11 | $10^6$ | 2+ | 2+ |
| 0.22 | $10^6$ | 1+ | 1+ |
| 0.44 | $10^6$ | — | — |
| 0.67 | $10^6$ | — | — |
| 0.89 | $10^6$ | — | — |
| 1.11 | $10^6$ | — | — |
| Control | $10^6$ | 4+ | NA |

An experimental apparatus is constructed similar in structure to the embodiment shown in FIG. 7 with the addition of an ultrasonic sprayer that introduces a *Bacillus pumilus* spore-containing spray into the air as it passes into the air duct, and with the addition of a collection plate positioned between the air duct and the exhaust duct for collecting the *Bacillus pumilus* spores after treatment.

The flashlamp is flashed at a pulse repetition rate of about 2.5 or about 5.0 flashes per second. About one second after the flashing of the flashlamp is commenced, the ultrasonic sprayer sprays 180 microliters (or 160 microliters in the case of the 5.0 flash per second pulse repetition rate) of spores into the air passing into the duct. After the spraying of the spores, the flashlamp is flashed for an additional 20 seconds insuring that the air duct is free of spores before ceasing flashing of the flashlamp. The air, which has a central line velocity of 0.5 meters per second, carries the spores through the treatment region past the flashlamp and into the exit region. Upon exiting the air duct, the spores are carried onto the collection plate located between the air duct and the exhaust duct.

On each set of experiments, several passes are conducted during which the ultrasonic sprayer sprays spores into the air stream, but the flashlamp is not flashed so as to provide a baseline measurement of deactivation of the spores.

The result of one set of experiments conducted in accordance with the methodology is presented in Table 3.

TABLE 3

| | Control (mean + std. dev.) | Flashing Control (mean + std. dev.) | Sample (mean + std. dev.) |
|---|---|---|---|
| 2.5 Hz | 112.5 ± 39 log 2.05 (+2.18/−1.86) | 126 ± 103 log 2.1 (+2.36/−1.36) | 0.0 ± 0 |
| 5.0 Hz | 123.1 ± 48 log 2.09 (+2.23/−1.87) | 114 ± 48 log 2.05 (+2.2/−1.82) | 0.0 ± 0 |

EXAMPLE IV

Lab jacks are initially set up for a 0.8 Joules/cm² fluence level (which results from a 120 millimeter distance between a quartz window and a flashlamp light source to a bottom quartz disc. A vial of Poliovirus is vigorously shaken. Using a 100 microliter pipettor a 150 microliter sample of the Poliovirus are transferred from the vial to a 1 millimeter space between a pair of quartz discs. The pair of discs is gently tilted until the 150 microliter sample is positioned near the center of the discs. The discs are then placed on the lab jack. For an untreated control sample, the discs are removed from the lab jack and the 150 microliter sample is withdrawn and placed in a sterile vial. For additional samples, two flashes at 0.8 Joules/cm² are delivered to the 150 microliter sample. Further samples are treated with two flashes at 0.6 Joules/cm², 0.4 Joules/cm² and 0.2 Joules/cm², by adjusting the lab jacks. The treated samples are respectively withdrawn and placed in sterile vials. The Polio virus suspensions are then quantitated using tissue culture plaque titer assays.

Table 4 presents results of virus assays.

TABLE 4

| Sample | Titer (plaque forming units/ml) |
|---|---|
| 0.8 J/cm² | $2.3 \times 10^2$ |
| 0.6 J/cm² | 85 |
| 0.4 J/cm² | $2.2 \times 10^4$ |
| 0.2 J/cm² | $1.6 \times 10^3$ |
| Control (non-treated) | $9 \times 10^8$ |

Thus, the above examples demonstrate the effectiveness of the methods described herein for deactivating microorganisms, such as cyst-forming protozoa, specifically *Cryptosporidium parvum*, in fluids such as water and air, and such as viruses, specifically Poliovirus.

While the invention herein disclosed has been described by means of specific embodiments and applications thereof, numerous modifications and variations could be made thereto by those skilled in the art without departing from the scope of the invention set forth in the claims.

What is claimed is:

1. A system for deactivating microorganisms in fluid comprising:

a watertight housing;

an inlet port of the watertight housing;

an outlet port of the watertight housing;

a light source positioned within the watertight housing;

a baffle positioned within the watertight housing for directing a substantially uniform flow of fluid in a direction substantially parallel to the light source;

a jacket surrounding the light source to provide a watertight barrier therearound; and a circulating cooling material between the jacket and the light source within the watertight barrier for cooling the light source.

2. The system of claim 1 wherein:

said baffle-has a first and a second end; and said inlet port and said outlet port are positioned proximate the second end of the baffle.

3. The system of claim 2 wherein:

said baffle directs said fluid from said inlet port in a direction substantially antiparallel to said light source, and directs said fluid to said outlet port in a direction substantially parallel to said light source.

4. The system of claim 3 wherein:

said inlet port is positioned to flow fluid into said watertight housing from outside said baffle; and said outlet port is positioned to withdraw fluid from said watertight housing from inside said baffle, said fluid flowing around said first end of said baffle.

5. The system of claim 1 wherein:

said light source is positioned substantially along a central axis of said baffle.

6. The system of claim 5 wherein:

said baffle is substantially cylindrical.

7. The system of claim 5 wherein:
said watertight housing is substantially cylindrical.

8. The system of claim 6 wherein:
an inner surface of the baffle is reflectorized for reflecting light emitted from the light source.

9. The system of claim 1 wherein said outlet port is oriented to expose an interior surface thereof to light emitted from the light source.

10. The system of claim 9 wherein said outlet port includes a frustoconical inner surface.

11. The system of claim 9 further comprising:
a removable recirculating hose in fluid communication with the inlet port and outlet port.

12. The system of claim 1 further comprising:
an annular baffle located near the inlet port whereby the annular baffle helps distribute the fluid flowing through the inlet port.

13. A system for deactivating microorganisms in fluid comprising:
a cylindrical watertight housing having a closed first end and a closed second end;
a coaxial cylindrical baffle positioned within the watertight housing with a space formed between them for fluid to flow in a first flow direction, the baffle having a closed second end attached to the second end of the watertight housing and an open first end terminating before the first closed end of the cylindrical housing forming a gap therebetween;
a coaxial tubular light source being positioned within the cylindrical baffle with a space formed between them for fluid to flow in a second flow direction;
an inlet port located in the closed second end of the cylindrical housing between the cylindrical housing and the cylindrical baffle;
an outlet port located in the second end of the cylindrical housing between the cylindrical baffle and the tubular light source whereby fluid enters the system through the inlet port traveling in the first flow direction between the cylindrical housing and cylindrical baffle, around the gap at the first end the cylindrical baffle and traveling opposite in the second flow direction between the cylindrical baffle and the tubular light source to the outlet port where the fluid exits the system;
a jacket surrounding the tubular light source to provide a watertight barrier therearound; and
a circulating cooling material between the jacket and the tubular light source within the watertight barrier for cooling the tubular light source.

14. The system of claim 13 wherein:
an inner surface of the cylindrical baffle is reflectorized for reflecting light emitted from the tubular light source.

15. The system of claim 13 further comprising:
an annular baffle located near the inlet port whereby the annular baffle distributes the fluid flowing through the inlet port to create a uniform flow dynamic in the first flow direction.

16. The system of claim 13 wherein
the jacket comprises a quartz jacket.

17. The system of claim 13 wherein:
the cooling material spectrally filters light from the tubular light source.

18. A system for deactivating microorganisms in fluid comprising:
a cylindrical watertight housing having a closed first end and a closed second end;
a coaxial cylindrical baffle positioned within the watertight housing with a space formed between them for fluid to flow in a first flow direction, the baffle having a closed second end attached to the second end of the watertight housing and an open first end terminating before the first closed end of the cylindrical housing forming a gap therebetween;
a coaxial tubular light source being positioned within the cylindrical baffle with a space formed between them for fluid to flow in a second flow direction;
an inlet port located in the closed second end of the cylindrical housing between the cylindrical housing and the cylindrical baffle;
an outlet port proximate the second end of the cylindrical baffle extending radially through a side of cylindrical housing, the outlet port being oriented to expose an interior surface thereof to light emitted from the light source whereby fluid enters the system through the inlet port traveling in the first flow direction between the cylindrical housing and cylindrical baffle, around the gap at the first end the cylindrical baffle and traveling opposite in the second flow direction between the cylindrical baffle and the tubular light source to the outlet port where the fluid exits the system;
a jacket surrounding the tubular light source to provide a watertight barrier therearound; and
a circulating cooling material between the jacket and the tubular light source within the watertight barrier for cooling the tubular light source.

19. The system of claim 18 wherein:
an inner surface of the cylindrical baffle is reflectorized for reflecting light emitted from the tubular light source.

20. The system of claim 18 wherein:
said outlet port includes a frustoconical inner surface.

21. The system of claim 18 further comprising:
an annular baffle located near the inlet port whereby the annular baffle distributes the fluid flowing through the inlet port to create a uniform flow dynamic in the first flow direction.

22. The system of claim 18 wherein
the jacket comprises a quartz jacket.

23. The system of claim 18 wherein:
the cooling material spectrally filters light from the tubular light source.

24. The system of claim 18 further comprising:
a removable recirculating hose in fluid communication with the inlet port and outlet port.

25. A system for deactivating microorganisms in fluid comprising:
a watertight housing having a first end and a second end;
an inlet port of the watertight housing;
an outlet port of the watertight housing;
a light source positioned within the watertight housing;
a baffle positioned within the watertight housing for directing a substantially uniform flow of fluid in a direction substantially parallel to the light source;
a jacket surrounding the light source;
a circulating cooling material between the jacket and the light source for cooling the light source;
a first lamp holder attached to the first end of the watertight housing; and
a second lamp holder attached to the second end of the watertight housing;
wherein the first and second lamp holders are each configured to provide access to the light source.

* * * * *

UNITED STATES PATENT AND TRADEMARK OFFICE
CERTIFICATE OF CORRECTION

PATENT NO. : 6,228,332 B1
DATED : May 8, 2001
INVENTOR(S) : Dunn et al.

It is certified that error appears in the above-identified patent and that said Letters Patent is hereby corrected as shown below:

<u>Column 16,</u>
Line 48, change "baffle-has" to -- baffle has --.

<u>Column 18,</u>
Line 18, after "end", insert -- of --.

Signed and Sealed this

Eighth Day of January, 2002

*Attest:*

JAMES E. ROGAN
*Attesting Officer*     *Director of the United States Patent and Trademark Office*